(12) United States Patent
Raby et al.

(10) Patent No.: US 7,210,929 B2
(45) Date of Patent: May 1, 2007

(54) METHOD OF ORIENTING AN ORTHODONTIC APPLIANCE TO A TOOTH

(75) Inventors: Richard E. Raby, St. Paul, MN (US); Oliver L. Puttler, La Crescenta, CA (US); Nicholas A. Stark, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 699 days.

(21) Appl. No.: 10/734,323

(22) Filed: Dec. 12, 2003

(65) Prior Publication Data

US 2005/0130095 A1    Jun. 16, 2005

(51) Int. Cl.
*A61C 3/00* (2006.01)
(52) U.S. Cl. ...................................... 433/24
(58) Field of Classification Search ............ 433/2, 433/3, 24
See application file for complete search history.

(56) References Cited

U.S. PATENT DOCUMENTS

| | | | |
|---|---|---|---|
| 4,014,096 A | 3/1977 | Dellinger | |
| 4,455,137 A | 6/1984 | Diamond | |
| 4,850,864 A | 7/1989 | Diamond | |
| 5,011,405 A | 4/1991 | Lemchen | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,431,562 A | 7/1995 | Andreiko et al. | |
| 6,089,868 A | 7/2000 | Jordan et al. | |
| 6,123,544 A | 9/2000 | Cleary | |
| 7,029,275 B2 * | 4/2006 | Rubbert et al. | ............. 433/24 |
| 7,033,327 B2 * | 4/2006 | Raby | ............. 600/590 |
| 7,080,979 B2 * | 7/2006 | Rubbert et al. | ............. 433/24 |
| 2002/0006217 A1 | 1/2002 | Rubbert et al. | |
| 2002/0028417 A1 | 3/2002 | Chapoulaud et al. | |
| 2002/0150859 A1 | 10/2002 | Imgrund et al. | |
| 2002/0156652 A1 | 10/2002 | Schdeva et al. | |
| 2003/0096210 A1 | 5/2003 | Rubbert et al. | |
| 2003/0143509 A1 | 7/2003 | Kopelman | |
| 2003/0224316 A1 * | 12/2003 | Marshall | ............. 433/24 |
| 2004/0142297 A1 * | 7/2004 | Taub et al. | ............. 433/3 |

FOREIGN PATENT DOCUMENTS

| | | |
|---|---|---|
| DE | 100 24 833 | 11/2001 |
| WO | WO 97/03622 | 2/1997 |
| WO | WO 02/24100 | 3/2002 |
| WO | WO 03/061507 | 7/2003 |

* cited by examiner

*Primary Examiner*—Ralph A. Lewis
(74) *Attorney, Agent, or Firm*—James D. Christoff

(57) ABSTRACT

The relative orientation of an orthodontic appliance and a tooth is selected by providing a first relative orientation between the appliance and the tooth, and defining a first set of hypothetical reference lines or rays between the base of the appliance and the tooth in virtual three-dimensional space. The distance along each ray is then determined. Next, the relative orientation of the appliance and the tooth is changed to a second orientation. A second set of rays is defined between the appliance and the tooth, and the distance along each ray is determined. A mathematical computation is then carried out on the determined distances in order to help determine whether the first orientation or the second orientation provides a better fit between the base of the appliance and the tooth surface.

41 Claims, 12 Drawing Sheets

METHOD OF ORIENTING AN ORTHODONTIC APPLIANCE TO A TOOTH

BACKGROUND OF THE INVENTION

1. Field of the Invention

This invention broadly relates to a method for orienting an orthodontic appliance, such as a bracket or buccal tube, to a tooth. More particularly, the present invention is concerned with a method for selecting the relative orientation of an orthodontic appliance that is adapted to be directly bonded to a tooth by an adhesive.

2. Description of the Related Art

Orthodontic treatment involves movement of malpositioned teeth to orthodontically correct locations. Orthodontic treatment can result in improved occlusion, so that the teeth properly function with other teeth in a satisfactory manner during mastication. Orthodontic treatment can also greatly enhance the aesthetic appearance of the patient's oral cavity.

One common type of orthodontic treatment involves the use of tiny appliances known as brackets that are often fixed to the patient's anterior, cuspid and bicuspid teeth. An archwire is placed in a slot of each bracket. The archwire forms a track to guide movement of the teeth to desired locations.

Ends of orthodontic archwires are often placed in passages of small appliances known as buccal tubes. In turn, the buccal tubes are fixed to the patient's molar teeth. The brackets, buccal tubes and archwires form an orthodontic system that is commonly known collectively as "braces".

One popular method of orthodontic treatment is known as the "level-arch" technique, and involves placing the brackets on the patient's teeth at certain selected locations so that the "U"-shaped archwire extends in a generally level plane at the conclusion of treatment. When the archwire is initially installed on the brackets, the malpositioned teeth may cause the wire to deviate from its normally planar configuration (in horizontal view) and from its normally smoothly curved configuration (in plan view). However, the inherent resiliency of the archwire tends to urge the brackets and hence the associated teeth toward a level array wherein the archwire re-assumes its normally planar and smoothly curved configuration. The level-arch technique is considered satisfactory by many orthodontists because the need for bends, steps or other adjustments in the archwire is reduced and in many cases eliminated, resulting in a savings of time for both the orthodontist as well as the patient.

As can be appreciated, the degree of success of the level-arch technique is related in part to the position and orientation of the brackets and buccal tubes on the patient's teeth. For example, if one of the brackets is bonded to a patient's tooth at a location that is too close to the patient's gingiva (i.e., the patient's gums) relative to the placement of brackets on adjoining teeth, that tooth will protrude outwardly an excessive distance in an occlusal direction (i.e., in a direction toward the outer tips of the patient's teeth) relative to adjoining teeth at the conclusion of treatment if all of the brackets are aligned in a level array. In such an instance, the orthodontist can correct the orientation of the malpositioned tooth by placing bends or steps in the archwire at locations adjacent each side of its bracket, but such a practice entails additional work for the orthodontist and may also increase the overall length of treatment time.

As a consequence, many suggestions have been made in the past for improving the placement accuracy of orthodontic appliances during the procedure of bonding the appliances to the patient's teeth. For example, height gauges such as the well-known "Boone" gauge provide a means for indicating a desired position of the appliance on a tooth relative to the occlusal edge of the associated tooth. Another device for improving placement accuracy is known as a positioning device or jig, such as the devices described in U.S. Pat. Nos. 4,455,137, 4,850,864 and 5,429,229. These devices support the appliance on a tooth surface at a location that is a pre-determined distance from the occlusal edge of the tooth.

While the bonding techniques described above are considered satisfactory by some practitioners, there are shortcomings that are inherent with such techniques. For example, access to the surfaces of certain malpositioned teeth (such as the bicuspid and molar teeth) may be difficult. In some instances, and particularly in connection with posterior teeth, the practitioner may have difficulty seeing the precise position of the appliance relative to the tooth surface. Another problem with the above described techniques concerns the significant length of time needed to carry out the procedure of positioning and bonding an appliance to each individual tooth, which is a nuisance both to the patient as well as to the orthodontist. The risk of moisture contamination from the patient's saliva also increases as the time increases that the patient is awaiting completion of the bonding procedure. The above factors may also unduly impair the accuracy of placement of the appliances on the teeth and/or increase the chance that the ultimate adhesive bond will not have sufficient strength to retain the appliances on the teeth during the course of orthodontic treatment.

Bonding techniques known as "indirect bonding" avoid many of the problems noted above. In general, indirect bonding techniques involve the use of a transfer tray having a shape that matches the configuration of at least part of one of the patient's dental arches. A set of appliances is releasably connected to the tray at certain, pre-determined locations. Once adhesive is applied to the base of each appliance, the tray is placed over the patient's teeth until such time as the adhesive hardens. Next, the tray is detached from the teeth as well as from the appliances, often with the result that all of the appliances that were previously connected to the tray are now bonded to their respective teeth at certain intended, pre-determined locations. The procedure is often then repeated for the patient's other dental arch.

In more detail, one known method of indirect bonding includes the steps of taking an impression of the patient's dental arch and then making a replica plaster or "stone" model from the impression. A sealing solution (such as Liquid Foil brand sealing solution from 3M) is applied to the stone model and allowed to dry. If desired, the teeth of the model are marked with a pencil to assist in placing the appliances in ideal positions.

Next, the appliances are temporarily bonded to the sealed stone model. Optionally, the bonding adhesive can be a chemical curing adhesive (such as Concise brand from 3M) or a light curable adhesive (such as Transbond XT or Transbond LR adhesive from 3M). Optionally, the appliances may be adhesive pre-coated brackets such as described in U.S. Pat. Nos. 5,015,180, 5,172,809, 5,354,199 or 5,429,229.

A transfer tray is then made by placing matrix material over the model as well as over the appliances on the model. For example, a plastic sheet matrix material may be placed over the model and appliances and then heated in an oven. A vacuum source is used to evacuate air between the matrix material and the model. As the matrix material is heated, the plastic sheet material is drawn down over the model and assumes a configuration that precisely matches the shape of the replica teeth of the stone model and adjacent appliances.

The plastic model is then allowed to cool and harden to form a tray. Next, the tray and the appliances (which are embedded in an interior wall of the tray) are detached from the stone model, and the sides of the tray are trimmed as may be desired. The tray also may be cut into smaller sections for ease of placement during bonding. If the cured adhesive remains on the appliance base after detaching the appliances from the model, the adhesive can serve as a custom-made bonding surface having a contour that matches the contour of the patient's tooth for a snug, mating fit.

Once the patient has returned to the office, a quantity of adhesive is placed on the base of each appliance (or on the cured adhesive, if any), and the tray (or tray section) with the embedded appliances is then placed over matching portions of the patient's dental arch. Since the configuration of the interior channel in the tray closely matches the respective portions of the patient's dental arch, each appliance is ultimately positioned on the patient's teeth at precisely the same location that corresponds to the previous location of the same appliance on the stone model.

Both light-curable adhesives and chemical curing adhesives have been used in indirect bonding techniques to secure the appliances to the patient's teeth. If a light-curable adhesive is used, the tray is preferably transparent or translucent. If a two-component chemical curing adhesive is used, the components can be mixed before application to the appliances, or alternatively one component may be placed on each appliance base (or on the cured adhesive, if any) and the other component may be placed on the tooth surface. In either case, placement of the tray with the embedded appliances on corresponding portions of the patient's dental arches enables the appliances to be bonded to the teeth as a group in a relatively short amount of time. With such a technique, individual placement and positioning of each appliance in seriatim fashion on the teeth is avoided.

U.S. Pat. No. 6,123,544, assigned to the assignee of the present invention, describes improved methods and apparatus for precisely positioning and bonding orthodontic appliances to the teeth. In one embodiment described in that patent, orthodontic appliances are releasably connected to arms that, in turn, are slidably received in passageways of a transfer tray. After the transfer tray is received on one of the patient's dental arches, the arms are moved along the passageways until the adhesive on the appliances comes into contact with the tooth surfaces. The arms provide a means for moving the appliances to certain pre-selected positions on the teeth.

In some of the embodiments described in U.S. Pat. No. 6,123,544, the transfer tray is made by placing analogs of the orthodontic appliances on replica teeth such as a stone model. Each analog is connected to a respective fixture arm, and a quantity of matrix material is then applied to both the replica dental arch and the fixture arms. After the matrix material has hardened, the fixture arms with the appliance analogs are replaced by carrier arms that are releasably connected to the selected appliances.

The resulting location of the orthodontic appliances on the patient's teeth according to the methods and apparatus described in U.S. Pat. No. 6,123,544 is determined in substantial part by the selected orientation of the appliance analog on the replica dental arch. One method of selecting this orientation can be carried out manually by, for example, drawing pencil lines along the replica teeth in a mesial-distal direction, optionally using one of the height gauges described above. As another option, an automated device such as a computer controlled robotic arm may be used to place the appliance analogs on the associated replica teeth, using software and digital information of the replica dental arch to select desired locations of the analogs and ultimately of the selected appliances.

There is a continuing need in the art to further increase the accuracy of placement of orthodontic appliances on the patient's teeth, so that the ultimate positions of the teeth at the conclusion of orthodontic treatment is identical to the positions sought by the orthodontist. In addition, it is desirable that any new method for selecting the orientation of an orthodontic appliance on a tooth be carried out by the use of computer software that would be useful in diagnosis and treatment planning as well as in subsequent manufacturing processes, such as in the fabrication of indirect bonding transfer trays as described above.

SUMMARY OF THE INVENTION

The present invention relates to improved methods for selecting the relative orientations of orthodontic appliances and corresponding teeth. The methods are particularly useful when implemented by software. The methods can be used in conjunction with treatment diagnosis and planning, where virtual replicas of the appliances are displayed on a computer screen along with a virtual replica of the patient's dental arch.

In brief, the relative orientation of an orthodontic appliance and a tooth is selected by providing a first relative orientation between the appliance and the tooth, and defining a first set of hypothetical reference lines or rays between the base of the appliance and the tooth in virtual three-dimensional space. The distance along each ray is then determined. Next, the relative orientation of the appliance and the tooth is changed to a second orientation. A second set of rays is defined between the appliance of the tooth and the distance along each ray is determined. A mathematical computation is then carried out on the determined distances in order to help determine whether the first orientation or the second orientation provides a better fit between the base of the appliance and the tooth surface.

The software can also be used for placement of the appliances on the teeth. For example, the software may be used to instruct a multi-axis pick-and-place robot to attach corresponding, real appliances to a physical model of the patient's dental arch. Once the appliances are placed on the physical model of the arch, an indirect bonding tray may be fabricated for subsequent transfer of the appliances to the patient's teeth.

As used herein, the "orientation" of the appliance shall mean its position along linear axes of movement (translation movement) and/or its orientation about rotational axes of movement (rotational movement).

In more detail, the present invention in one aspect relates to a method of selecting a relative orientation of an orthodontic appliance and a tooth. The method includes:

providing a first relative orientation of the appliance and the tooth;

defining a first set of rays extending between a base of the appliance and the tooth when the appliance and the tooth are in the first relative orientation;

determining the distance along each ray between the base and the tooth when the appliance and the tooth are in the first relative orientation;

relatively moving the appliance and the tooth in an arc about a reference axis to a second relative orientation;

defining a second set of rays extending between the base and the tooth when the appliance and the tooth are in the second relative orientation;

determining the distance along each ray between the base and the tooth when the appliance and the tooth are in the second relative orientation;

quantifying the difference between the distances determined when the appliance and the tooth are in the first relative orientation and the distances determined when the appliance and the tooth are in the second relative orientation; and relatively moving the appliance and the tooth in an arc about the reference axis in a direction such that the quantified difference is reduced.

Another aspect of the invention is also directed to a method of selecting a relative orientation of an orthodontic appliance and a tooth. The method comprises:

providing a first relative orientation of the appliance and the tooth;

defining a first set of rays extending between a base of the appliance and the tooth when the appliance and the tooth are in the first relative orientation;

determining the distance along each ray between the base and the tooth when the appliance and the tooth are in the first relative orientation;

providing a second relative orientation of the appliance and the tooth;

defining a second set of rays extending between the base and the tooth when the appliance and the tooth are in the second relative orientation;

determining the distance along each ray between the base and the tooth when the appliance and the tooth are in the second relative orientation; and comparing the distances when the appliance and the tooth are in the first relative orientation to the distances when the appliance and the tooth are in the second relative orientation in order to select the orientation that corresponds to a closer fit between the base of the appliance and the tooth.

An additional aspect of the present invention is also directed toward a method of selecting a relative orientation of an orthodontic appliance and a tooth. This method comprises:

defining a set of rays extending between the appliance and a tooth, wherein each ray extends from a point located on the base of the appliance and the point located on the tooth;

determining the distance along the rays between each point on the base and each corresponding point on the tooth; and relatively moving the appliance and the tooth in an arc about a reference axis in a direction such that the sum of the differences between each distance and the mean of the distances is reduced.

The invention is also directed to computer readable storage medium having program code stored thereon. When a computer executes the program code, it carries out one or more of the methods mentioned above.

These and other aspects of the invention will be described in more detail below and are illustrated in the accompanying drawings.

DETAILED DESCRIPTION OF THE PREFERRED EMBODIMENTS

FIG. 1 is a block diagram showing various acts of a method for selecting a relative orientation of an orthodontic appliance on a orthodontic patient's tooth according to one embodiment of the invention. The method is particularly advantageous when used as a computer program. However, certain acts set out in the block diagram may be carried out manually if desired.

The method described in FIG. 1 includes the act in Block 20 of obtaining three-dimensional data that defines a surface of a dental arch. The surface of the dental arch may include all of the teeth of the upper or lower dental arch, or only some of the teeth of the upper or lower arch. Preferably, the surface includes all exposed sections of the dental arch with all of the sides of each tooth including the buccolabial side (i.e., the side facing the patient's lips or cheeks), the lingual side (i.e., the side facing the patient's tongue), the occlusal side (i.e., the side extending along the outer tip of each tooth), the mesial side (i.e., the side facing the middle of the patient's dental arch) and the distal side (i.e., the side facing away from the middle of the patient's dental arch). However, one or more sides of the teeth may be omitted if desired.

The data obtained in Block 20 may be obtained by any suitable means known in the art. For example, data representative of the teeth may be created by using a scanner such as an intra-oral camera that is held in the patient's oral cavity, or an X-ray apparatus or other type of radiation apparatus. Alternatively, a set of digital data may be obtained by the use of a contact probe that engages the surface of the patient's dental arch at a multitude of locations.

As another alternative, the data representative of the patient's teeth may be obtained by first taking an impression of the patient's teeth using a curable impression material. Next, digital data is obtained by scanning the impression with a camera or other device, or by use of the apparatus described in PCT Publication No. WO97/03622, which is expressly incorporated by reference herein. As another option, a model (such as a stone model) may be made from the resulting impression, and the data may then be obtained by scanning the model with a scanner such as a video camera, a laser scanner, by using a mechanical profilometer that mechanically probes the model, or by use of the apparatus described in PCT Publication WO97/03622. Other options for obtaining digital data are described in U.S. Pat. No. 6,123,544, which is expressly incorporated by reference herein.

The scanner may be directly coupled to a port of a data processor. Alternatively, the scanner may be located at a remote location and may communicate the scanned data to the data processor by way of a network interface.

Figure 3:
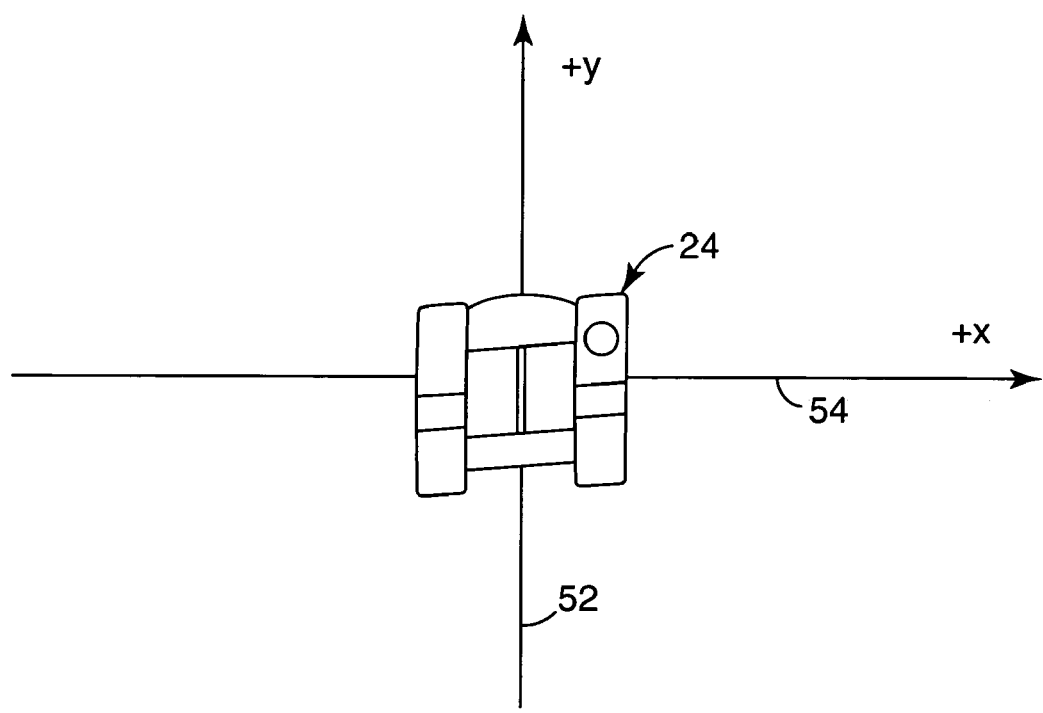
FIG. 3 is an elevational view, looking in a lingual direction, of an exemplary orthodontic appliance that may be used in the method set out in FIG. 1, additionally showing a pair of reference axes that have been placed in a certain orientation relative to the appliance.
Figure 4:
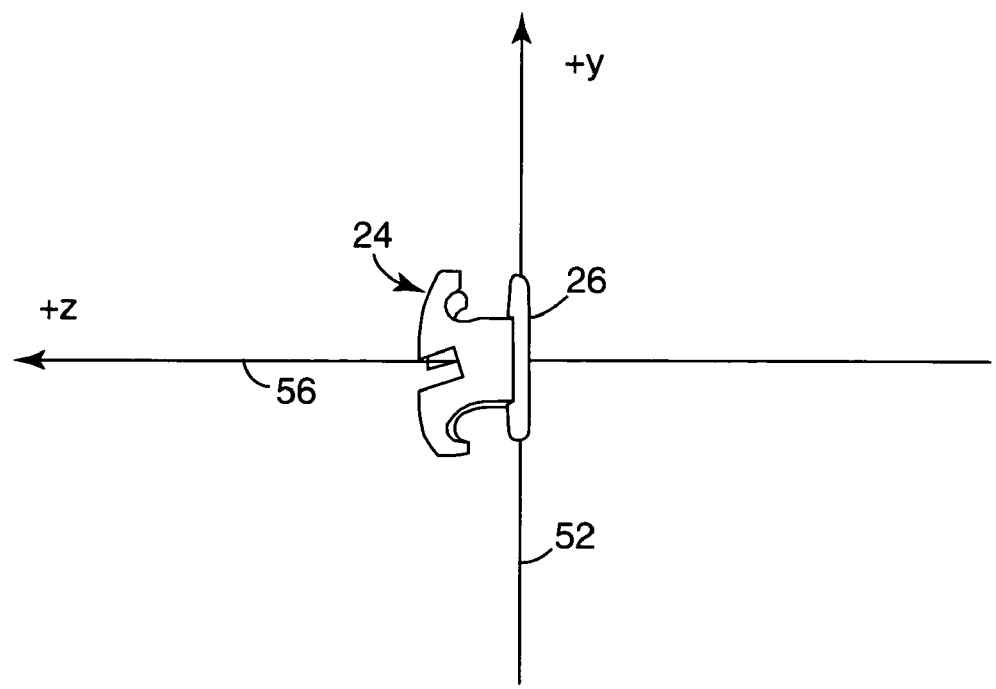
FIG. 4 is a side elevational view, looking in a mesial direction, of the appliance shown in FIG. 3 along with two reference axes.
Figure 6:
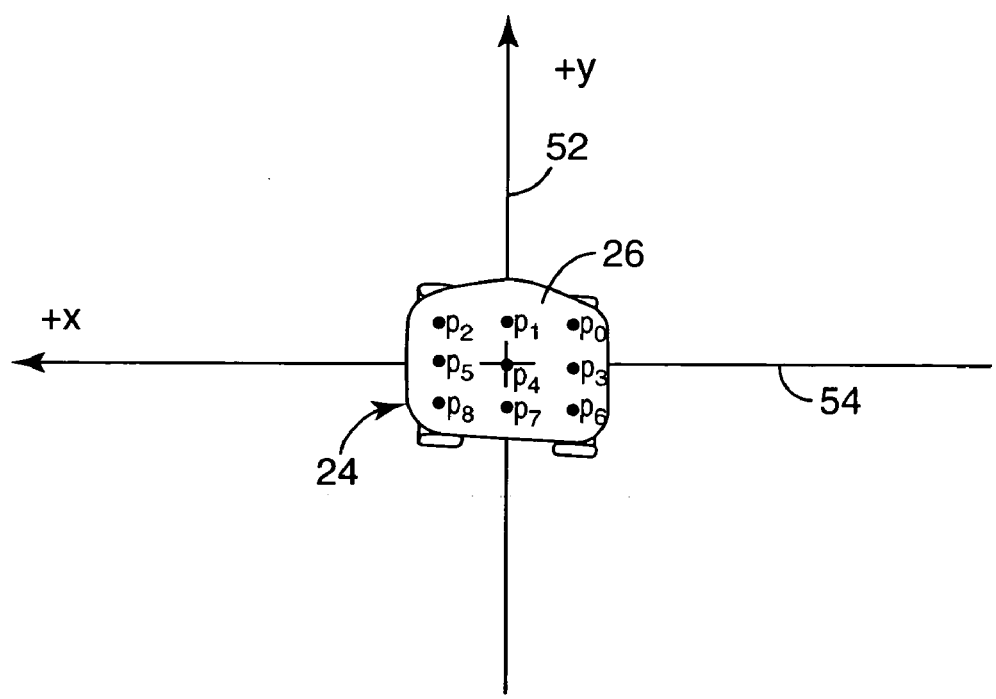
FIG. 6 is a rear elevational view, looking in a buccolabial direction, of the appliance shown in FIGS. 3 and 4, additionally showing for exemplary purposes nine points that have been designated on a base of the appliance.

As indicated by Block 22, three-dimensional data of a surface of an orthodontic appliance is also obtained. The appliance may be any orthodontic component that is adapted to be directly bonded to a tooth by use of an adhesive. Examples of such appliances include brackets, buccal tubes, buttons, cleats, lingual sheaths and bite planes. An example of a suitable orthodontic appliance is the bracket 24 that is shown in FIGS. 3, 4 and 6.

The three-dimensional data of the appliance that is described in Block 22 may be obtained by scanning the appliance with a camera or laser scanner. Preferably, however, the data is obtained from manufacturing data used to manufacture the appliance, such as a set of digital data used in automated milling machines.

Preferably, the three-dimensional data represents all exposed sections of the appliance surface, so that a visual representation of the appliance may be displayed to the practitioner as depicted in the drawings. Optionally, however, the surface may be limited to a base surface or base section of the appliance. In FIGS. 4 and 6, the base is indicated by the numeral 26.

Conventionally, the manufacturers of orthodontic appliances attempt to make the base of directly-bonded orthodontic appliances with a shape that is similar to the expected shape of a patient's tooth, using statistical averages, in an attempt to ensure that a close, mating fit between the appliance and the tooth is obtained. Oftentimes, the shape of the base represents a compound contour that is curved along two reference axes (such as a mesial-distal reference axis and an occlusal-gingival reference axis). However, some appliances, and particularly appliances adapted for bonding to the anterior teeth, may have a shape that is flat or essentially flat.

The base of many conventional orthodontic appliances is often textured to increase the bond strength between the appliance and the adhesive. The texture may be provided by roughening the base (for example, by sandblasting the base) or by providing projections, pores, recesses, dimples or other structure integral with or otherwise connected to the body of the appliance. As another alternative, the base of the appliance may be provided with a wire mesh, similar to a screen mesh with small openings. As yet another option, the base may be provided with a number of regular or irregular particles that project outwardly for contact with the adhesive.

In instances where the appliance does not have a base surface that is relatively smooth, such as in appliances mentioned in the preceding paragraph, the set of data for the appliance base may be obtained by creating a hypothetical, smoothly curved surface. The hypothetical surface is obtained by a best fit method, such as a method that provides a curved surface touching the outer extremity of a majority of projections. Other methods of obtaining a hypothetical curved surface may also be used.

As indicated by Box 28, a set of sample points, each defined in three-dimensional space, is obtained from the three-dimensional data representing the surface of the appliance base. The sampling of points is sufficient in number and distribution to at least roughly characterize the configuration and size (i.e., length and width) of the base. At a theoretical minimum, at least three points are needed. An example of a suitable number of points for an orthodontic appliance with a curved base is fifty. More points can be obtained in order to obtain a more accurate result, although the speed of carrying out the method may be hampered by the limitations of computer hardware.

For exemplary purposes, nine sample points designated $p_0$ to $p_8$ are shown in FIG. 6. Each of the points $p_0$ to $p_8$ lies on the surface of the base that is obtained in Block 22. Preferably, and as shown, some of the points lie adjacent the edge of the base 26 while at least one point lies near or on the center of the base 26. In the example shown in FIG. 6, point $p_4$ coincides with the center of the base 26.

Figure 5:
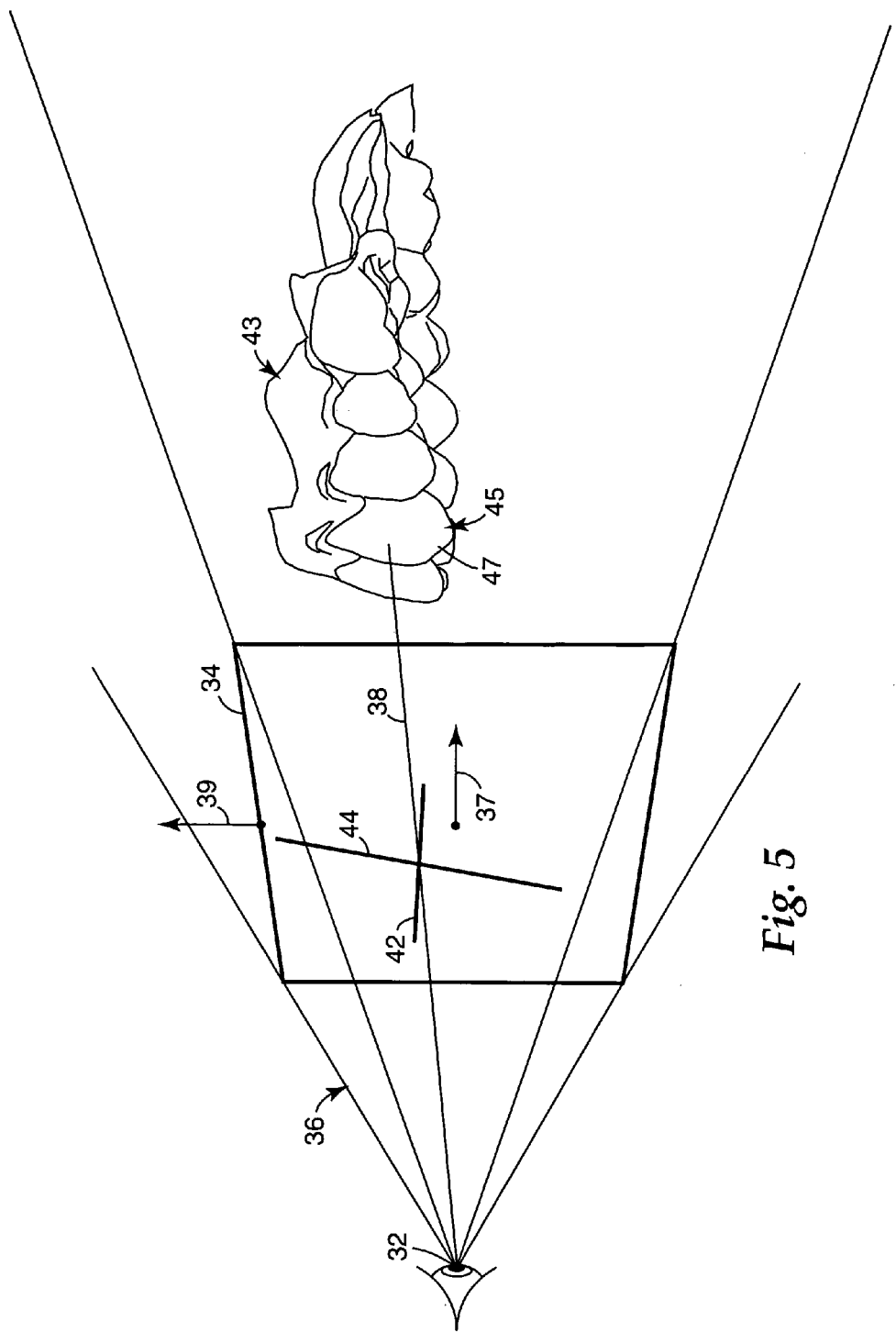
FIG. 5 is a schematic view illustrating an exemplary view-plane that is established in the method of FIG. 1.

A view frustum is then defined as indicated by Block 30 and as schematically illustrated in FIG. 5. An eye point 32 as shown in FIG. 5 represents the apex of the cone defined by the frustum. A two-dimensional view plane 34 is also defined and coincides with one surface of the frustum. The view frustum is designated by the numeral 36 in FIG. 5 and may be of any convenient shape (such as a four-sided pyramid or a right circular cone).

FIG. 5 also depicts a view plane normal vector 41a. The vector 41a extends in a direction perpendicular to the view plane 34 and optionally passes through the eye point 32. A view plane up vector 41b is also established. The view plane up vector 41b is parallel to the view plane 34 and extends in an upward direction when viewed by an observer. If, for example, the view plane 34 is rectangular, the view plane up vector 41b may be parallel to the left and right edges of the view plane 34, although other orientations are also possible. The view frustum 36 is then oriented relative to the dental arch so that the area of the arch that is intended to receive the appliance is projected onto the view plane. This is set out in Box 39.

Next, and as described in Box 40, a horizontal crosshair 42 and a vertical crosshair 44 are defined on the view plane 34. Preferably, the intersection of the horizontal and vertical crosshairs 42, 44 lies within the bounds of the view plane 34. However, the horizontal crosshair 42 and the vertical crosshair 44 need not actually lie horizontally and vertically, respectively, relative to the view plane up vector 41b, nor do they need to form a right angle between them.

The line-of-sight 38 is then defined as a ray that originates at the eye point 32, extends to the view plane 34 and passes through the intersection point of the crosshairs 42, 44. If, for example, the view frustum is a right rectangular pyramid or a right circular cone, and the crosshairs 42, 44 are placed at the center of the view plane, the line-of-sight 38 will be parallel to the view plane normal vector 43. However, other view frustums may be used, and in those instances the line-of-sight need not be parallel to the view plane normal vector 43.

The crosshairs 42, 44 are then oriented in the view plane 34 so that (1) the intersection of the crosshairs 42, 44 projects onto the surface of the dental arch at a location where the center of the surface of the appliance base 26 is desired, and (2) the rotative orientation of the crosshairs 42, 44 matches the rotative orientation desired of the bracket 24 about its buccolabial-lingual axis with respect to the dental arch. This act is described in Box 48. In practice, this orientation may be achieved by use of a user controlled computer input device such as a mouse or stylus to move the crosshairs 42 relative to the virtual arch.

Figure 1A:
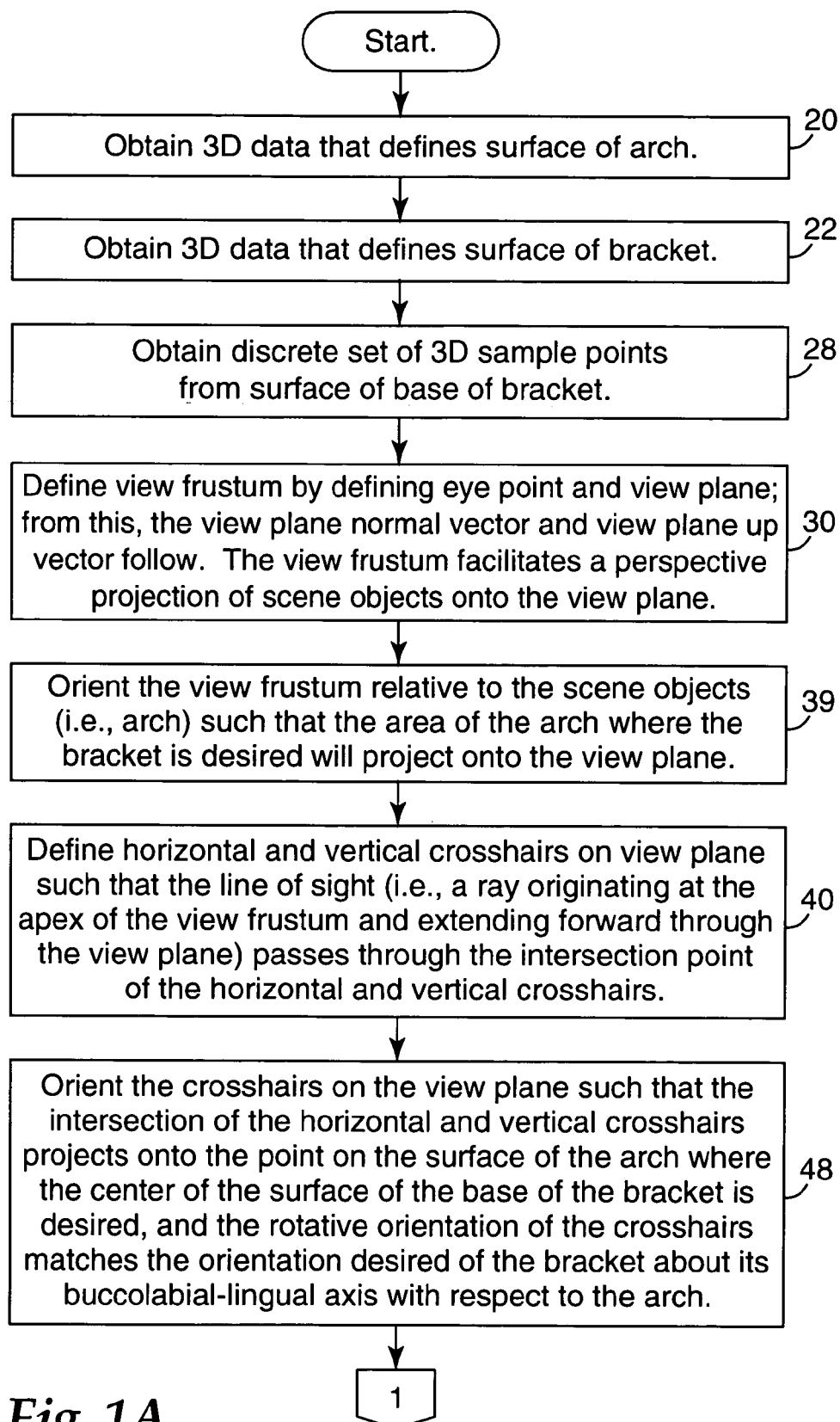
FIGS. 1a–1e collectively depict a flow chart describing a method of selecting a relative orientation of an orthodontic appliance and a tooth according to one embodiment of the present invention.
Figure 1B:
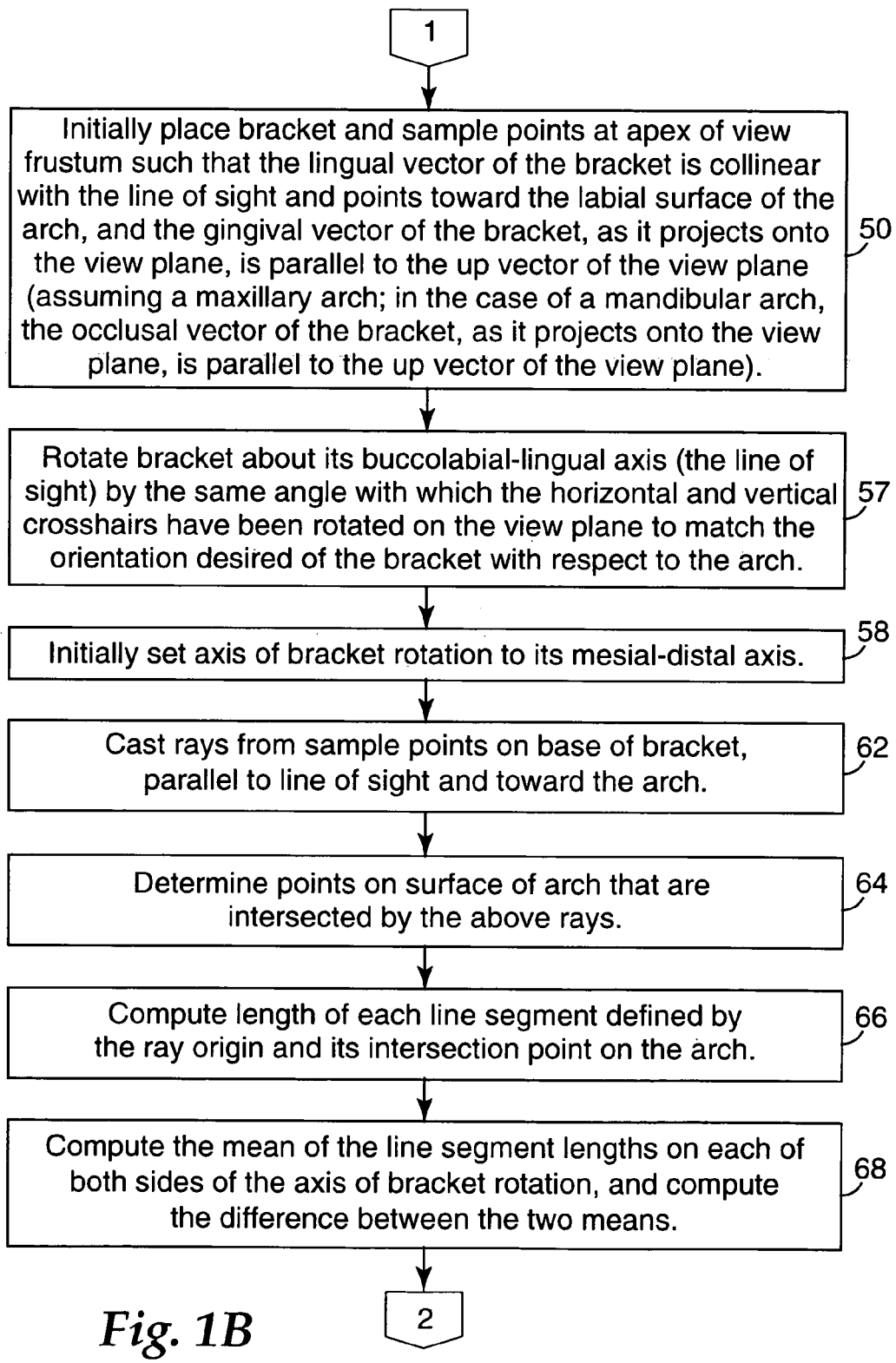
Figure 1C:
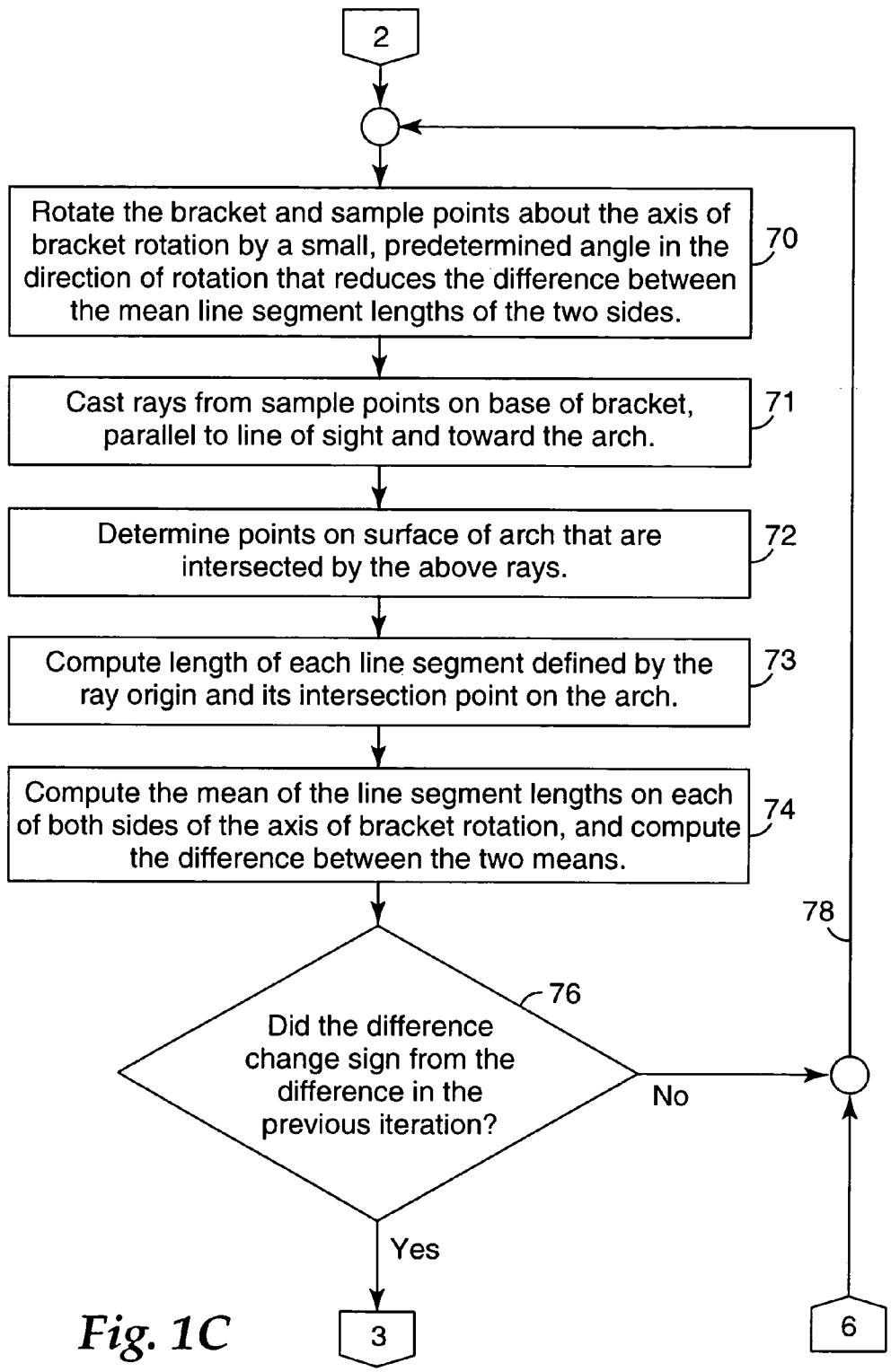
Figure 1D:
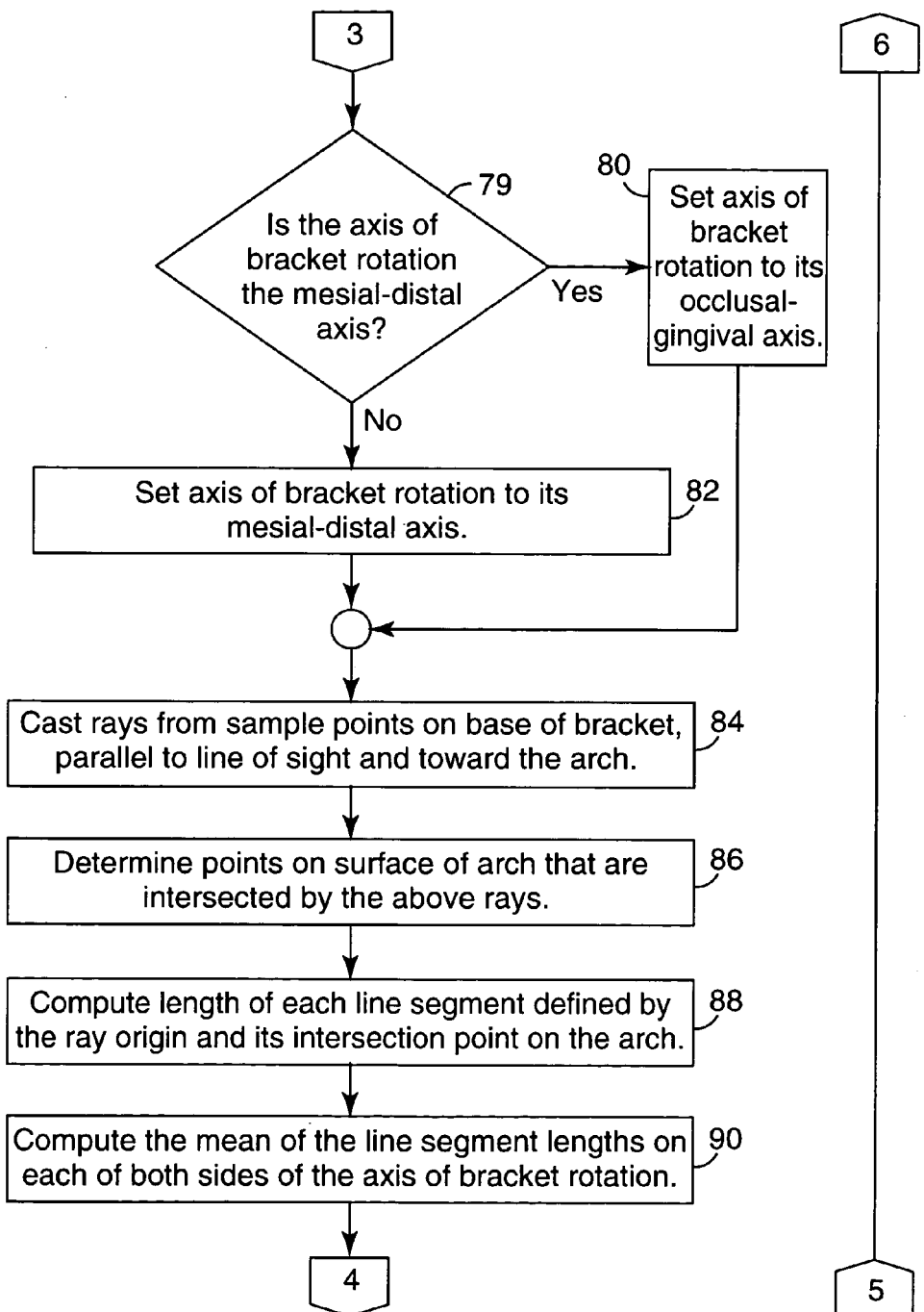
Figure 1E:
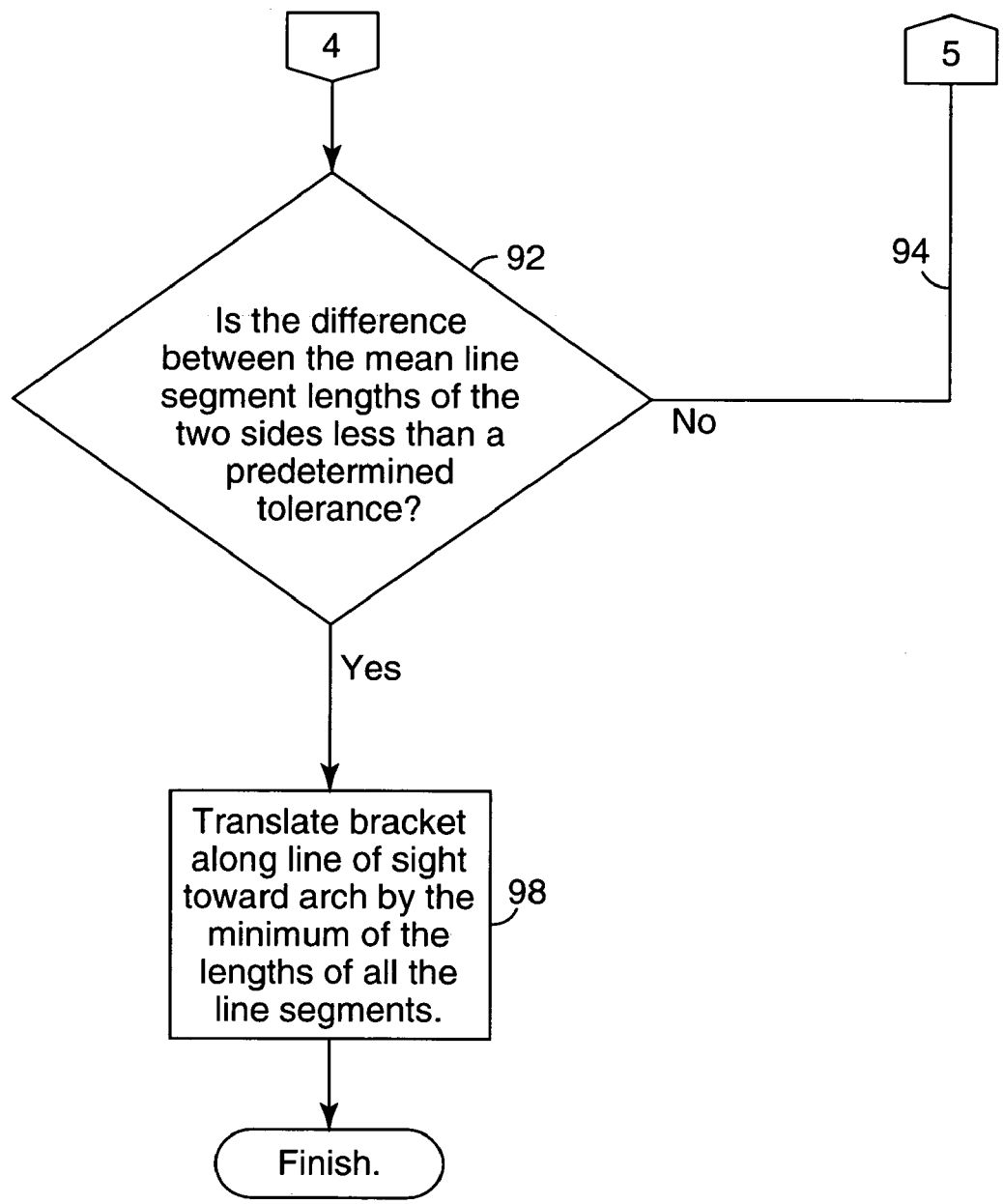
Figure 2:
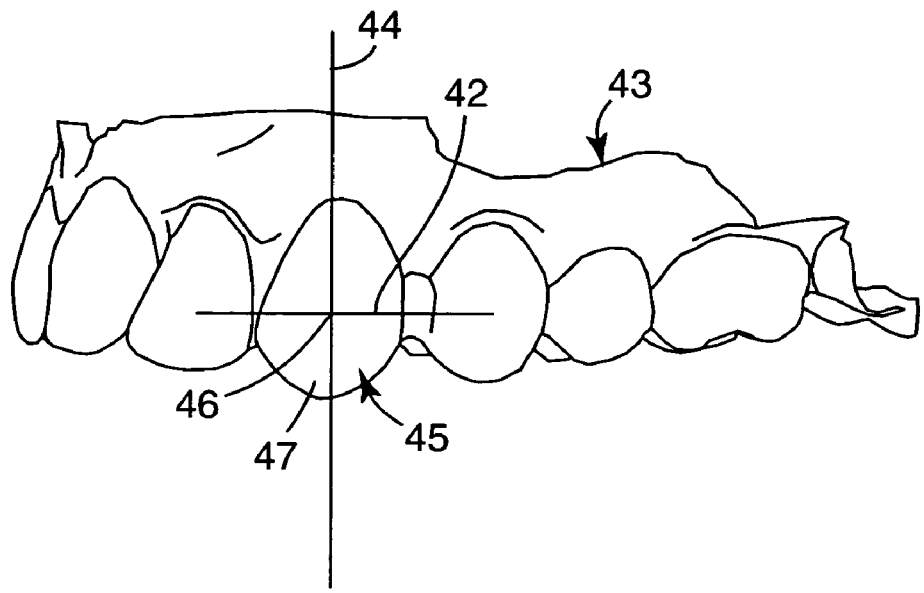
FIG. 2 is a schematic illustration looking in a lingual direction of a virtual representation of a patient's dental arch, additionally showing reference axes that have been placed in alignment with a cuspid tooth of the virtual model.

FIG. 2 illustrates a model of a patient's upper dental arch 43 that includes an upper left cuspid tooth 45 having a facial or buccolabial surface 47. In FIG. 2, the crosshairs 42, 44 have been aligned with a location on the model of the patient's upper left cuspid tooth 45. The particular location on the cuspid tooth 45 may be any location according to the particular orthodontic treatment plan desired by the orthodontic practitioner.

For example, the location on the tooth that is selected for alignment with the intersection of the crosshairs 42, 44 may coincide with the facial axis point 46 of the clinical crown of the cuspid tooth 45 as shown in FIG. 2. The facial axis point is located at the intersection of the mid-sagittal plane of the cuspid tooth 45 and the mid-lateral plane of the cuspid tooth 45 at a point where the intersection of the planes meets the buccolabial tooth surface.

Figure 2A:
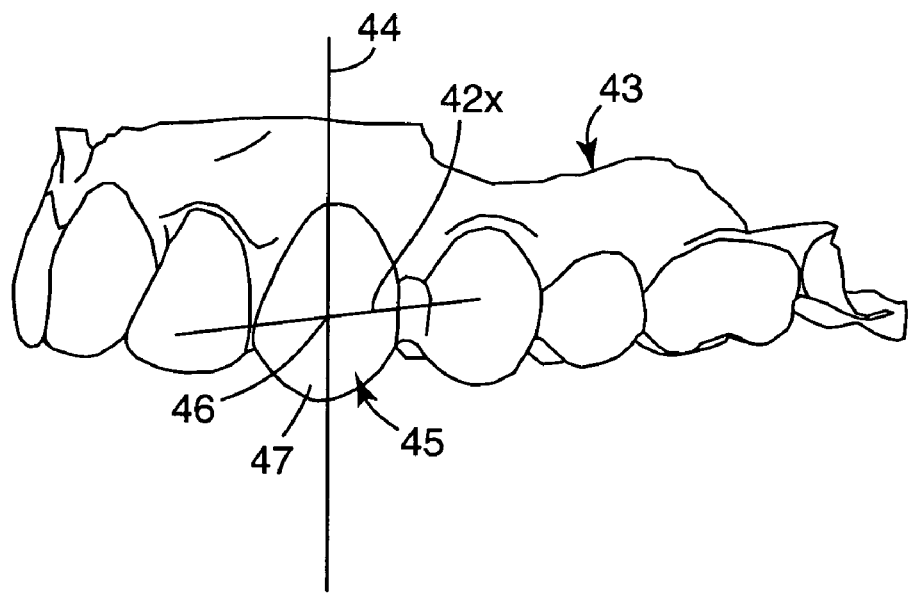
FIG. 2a is an illustration somewhat similar to FIG. 2, but showing another embodiment of the invention.

As an alternative, the crosshairs 42, 44 need not be perpendicular to each other. In FIG. 2a, the crosshair 42× extends at an angle other than 90 degrees relative to the crosshair 44. Such a practice may be desirable in instances where the selected bracket is angulated (i.e., the longitudinal axis of the archwire slot is not perpendicular to the mesial and distal sides of the bracket).

The bracket 26 is provided with three reference axes that are depicted in FIGS. 3 and 4. These three axes include an occlusal-gingival reference axis 52, a mesial-distal reference axis 54 and a buccolabial-lingual reference axis 56.

Next, the bracket 24 is placed at a point along the line-of-sight, preferably on the labial side of the tooth if the bracket 24 is to be placed labially, or preferably on the lingual side of the tooth if the bracket 24 is to be placed lingually. For example, and as set out in Box 50, the bracket 24 may be virtually placed at the apex of the view frustum 36 such that the bracket base 26 faces the labial surface of the cuspid tooth 45. The bracket 24 is also oriented so that a lingual vector of the buccolabial-lingual reference axis 56 is collinear with the line-of-sight. In addition, the bracket 24 is oriented such that the gingival vector of the occlusal-gingival reference axis 52, as it is projects onto the view plane 34, is parallel to the up vector 41b of the view plane 34 in instances when the arch is a maxillary arch. When the arch is a mandibular arch, the occlusal vector of the occlusal-gingival reference axis 52 is parallel to the up vector 41b of the view plane 34.

The bracket 24 is then rotated about its labio-lingual axis (i.e., the line-of-sight) as described in Box 57. The bracket 24 is rotated by the same angle with which the horizontal and vertical crosshairs 42, 44 have been rotated on the view plane 34 to match the orientation desired of the bracket 24 with respect to the dental arch 43.

Figure 8:
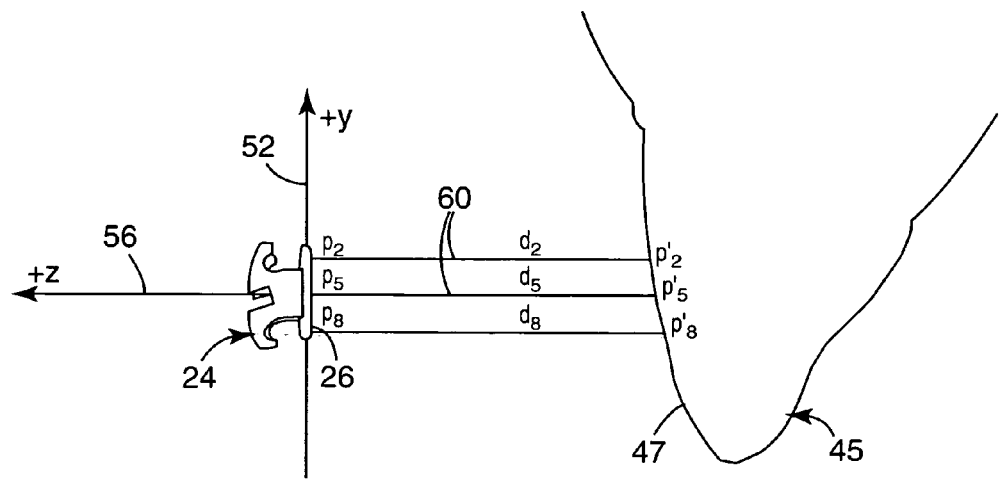
FIG. 8 is an enlarged side elevational view, looking in a mesial direction, of the appliance shown in FIGS. 3, 4 and 6 and the cuspid tooth alone that is illustrated in FIG. 7, additionally depicting three rays that extend between three of the points established on the base of the appliance and three corresponding points that have been established on the facial surface of the cuspid tooth.

Next, a first axis for rotation of the bracket 24 is selected. In this embodiment, and as indicated by Box 58, the mesial-distal reference axis 54 (FIG. 3) is first selected as an axis for rotation of the bracket 24. A set of reference lines or rays 60 are then established as described in Box 62. Each ray 60 extends from one of the sample points $p_0$ to $p_8$ toward the cuspid tooth 45. The rays 60 are illustrated in FIG. 8.

In the illustrated embodiment, the rays 60 extend parallel to one another and parallel to the line-of-sight toward the cuspid tooth 45. However, other methods are possible. For example, the rays 60 could radiate outward from a reference point such that a certain angle of divergence is present between the rays 60. Optionally, that reference point could coincide with the center of curvature of the base 26. As an additional option, a base 26 having a compound curvature might have two or more of such reference points.

Figure 7:
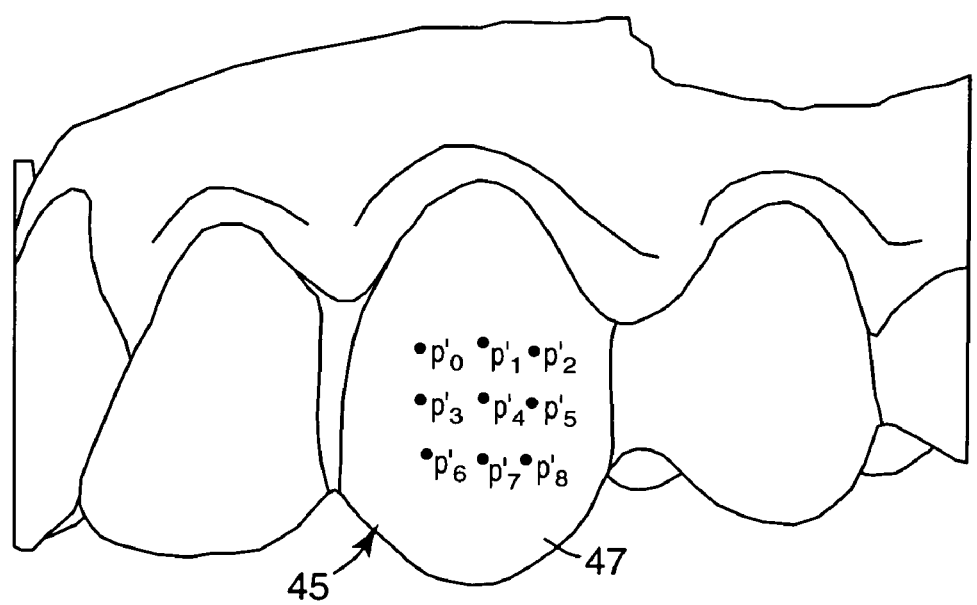
FIG. 7 is an enlarged, schematic, front elevational view of the virtual dental arch depicted in FIG. 2, additionally showing for exemplary purposes nine points that have been designated on a facial surface of the virtual cuspid tooth.

The method then involves the determination of points on the surface of the cuspid tooth 45 that correspond to locations where the rays 60 intersect the facial surface 47 of the tooth 45. This determination is described in Box 64. The points on the surface of the cuspid tooth 45 are designated $p'_0$ to $p'_8$ in FIGS. 7 and 8.

Next, and as indicated by Box 66, the distance is determined along each of the rays 60 between the bracket 24 and the tooth surface 47. Three of those distances are illustrated in FIG. 8 and are represented as $d_2$, $d_5$ and $d_8$. The distance $d_2$ represents the distance between points $p_2$ and $p'_2$, the distance $d_5$ represents the distance between point $p_5$ and $p'_5$, and so on.

Subsequently, an arithmetic function is carried out on some and preferably all of the distances determined in Block 66. For example, and as set out in Block 68, the mean distance of the distances determined in Block 66 on each side of the axis of rotation of the bracket 24 is separately calculated. For instance, if the mesial-distal axis passes through point $p_4$ of the base 26, the mean of the distances $d_0$, $d_1$, $d_2$ and $d_5$ is calculated. Additionally, the mean of the distances $d_3$, $d_6$, $d_7$ and $d_8$ is also calculated. The difference between those two means is then determined.

Other arithmetic functions are also possible. For example, the function could be a simple summation of the distances corresponding to the rays that lie on each side of the axis of rotation (in this instance, the mesial-distal axis). As another option, the arithmetic function may be a calculation of the root mean square of the distances that lie along each side of the axis of rotation. As yet another option, the arithmetic function may be a computation of the sum of the root mean squared errors between each distance $d_0$ to $d_8$ and the mean distance when considered over the entire base 26. In the latter option, the bracket 24 would be rotated about the axis of rotation in a direction that reduces the sum of the mean squared errors when compared with the sum of the mean squared errors from the previous orientation. As still another option, the arithmetic function may include a calculation of the volume of at least a portion of the space between the base and the tooth, preferably using a calculation that includes one of the distance calculations mentioned above.

The bracket 24 and the cuspid tooth 45 are then moved relative to each other from the previous orientation (e.g., a "first" orientation) to a second orientation that is different from the first orientation as described in Box 70. For example, the bracket 24 may be moved to a second orientation while the cuspid tooth 45 remains stationary. As another option, the bracket 24 may remain stationary while the cuspid tooth 45 moves.

Figure 9:
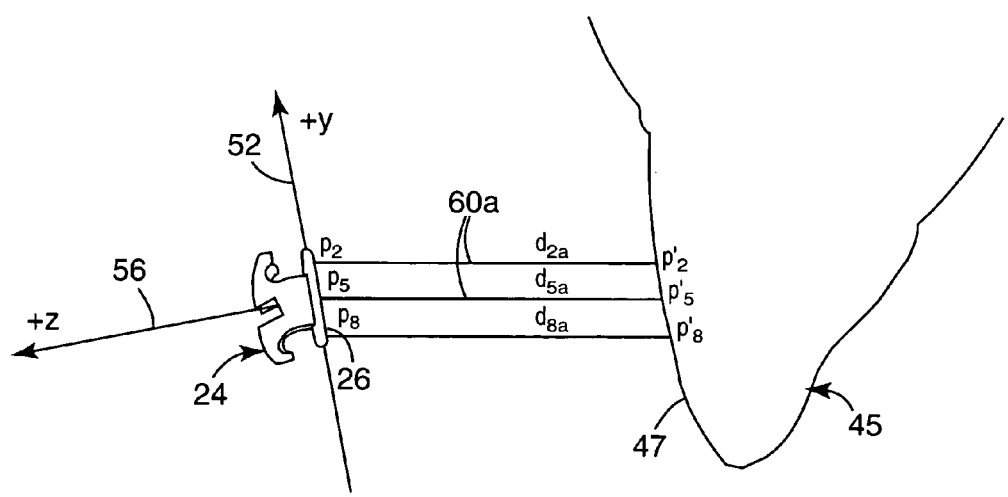
FIG. 9 is a view somewhat similar to FIG. 8 except that the relative orientation of the appliance and the tooth has been changed.

For example, and as shown by a comparison of FIGS. 8 and 9, the bracket 24 is rotated about its mesial-distal axis 54 from the first orientation shown in FIG. 8 to the second orientation shown in FIG. 9. The rotative movement is preferably carried out in a small, predetermined angular increment in a direction that reduces the difference between the mean distances calculated in Box 68. Although the orientation of the bracket 24 to the tooth 45 has now been changed, the points $p_0$ to $p_8$ remain in the same location on the base 26.

Next, a set of reference lines or rays 60a are established as set out in Box 71. Each ray 60a extends from one of the sample points $p_0$ to $p_8$ toward the cuspid tooth 45. In this embodiment, the rays 60a extend parallel to each other and to the line-of-sight toward the tooth 45 as shown in FIG. 9.

The method then involves the determination of points on the surface of the cuspid tooth 45 that correspond to locations where the rays 60a intersect the facial surface 67 of the tooth 45. This determination is described in Box 72. In FIG. 9, three points on the facial surface 47 are shown and are designated by the numerals $p'_{2a}$, $p'_{5a}$ and $p'_{8a}$.

The distance along the rays 60a between each point on the base 26 and the corresponding point on the cuspid tooth 45 when the tooth is in the second orientation is then determined as indicated by Box 73. This calculation is somewhat similar to the calculation set out in Box 66. In FIG. 9, the distances $d_{2a}$, $d_{5a}$ and $d_{8a}$ are exemplified.

Subsequently, the mean of the distances between the points and along the rays 60a on each side of the axis of rotation of the bracket 24 is determined for the second orientation of the tooth. This calculation is set out in Box 74 and is similar to the calculation mentioned above in connection with the first orientation of the tooth as set out in Box 68. Box 74 also includes the act of determining the differences of the two means.

The difference between the distances determined when the bracket 24 and the tooth 45 are in the first relative orientation and the distances determined when the bracket 24 and the tooth 45 are in the second relative orientation is then quantified. Subsequently, the bracket 24 and the tooth 45 are relatively moved in an arc about the reference axis in a direction such that the quantified difference is reduced. As an alternative description of the invention, the distances determined when the bracket 24 and the tooth 45 are in the first relative orientation and the distances determined when the bracket 24 and the tooth 45 are in the second relative orientation are compared in order to select the orientation corresponding overall to the smaller distances under a pre-selected mathematical computation, so that the direction of subsequent relative movement of the bracket 24 and the tooth 45 can be ascertained.

For example, and as set out in Box 76, the difference of the means calculated in Box 68 is then compared to the difference of the means calculated in Box 74. If the resulting difference did not change in sign, the method returns via path 78 to a location in the method immediately before Box 70 and the tasks described above are repeated. If the sign did change, the method proceeds to Box 79.

In Box 79, the axis of bracket rotation is recalled. If the axis of rotation identified in Box 70 was the mesial-distal reference axis 54, the method proceeds to Box 80, where the axis of rotation is changed to the occlusal-gingival reference axis 52. However, if the axis of bracket rotation identified in Box 70 was not the mesial-distal reference axis 54, the method proceeds to Box 82 where the axis of bracket rotation is set to the mesial-distal reference axis 54. From either Box 80 or Box 82, the method proceeds to Box 84.

As described in Box 84, a set of rays is extended from sample points on the base 26 of the bracket 24 in a direction toward the cuspid tooth 45. Optionally, the rays are parallel to each other and parallel to the line-of-sight. Preferably, each ray extends from the sample points previously identified on the bracket base 26 such as points $p_0$ to $p_8$. Each ray intersects the surface 47 of the cuspid tooth 45 at a point.

Box 86 represents the determination of the location of the points on the surface of the cuspid tooth 45. The length of each line segment between the points is then determined as described in Box 88. In particular, the distance between each sample point on the base 26 and the corresponding point on the surface of the cuspid tooth 45 is calculated.

Subsequently, the mean of the distances determined in Box 88 on each side of the axis of bracket rotation is calculated and the difference between the two means is computed. This calculation is indicated by Box 90 and is similar to the calculation set out in Box 68. However, the axis of bracket rotation in this instance may be the occlusal-gingival axis 52 (if proceeding from Box 80) or may be the mesial-distal reference axis 54 (if proceeding from Box 82).

The method then proceeds to Box 92. If the difference in mean distances that are calculated in Box 90 is greater than a predetermined tolerance, the method returns via paths 94 and 78 to the location immediately preceding Box 70. However, if the difference between the mean distances calculated in Box 90 is less than a predetermined tolerance, additional rotations are not needed and the method proceeds via path 96 to Box 98.

The bracket 24 is then translated along the line-of-sight toward the cuspid tooth 45 as described in Box 98. The bracket advances toward the cuspid tooth 45 a distance that is equal to the minimum distance determined in Box 88. Optionally, translation of the bracket toward the cuspid tooth 34 may be reduced by the expected thickness of adhesive used to bond the bracket 24 to the tooth surface.

Figure 10:
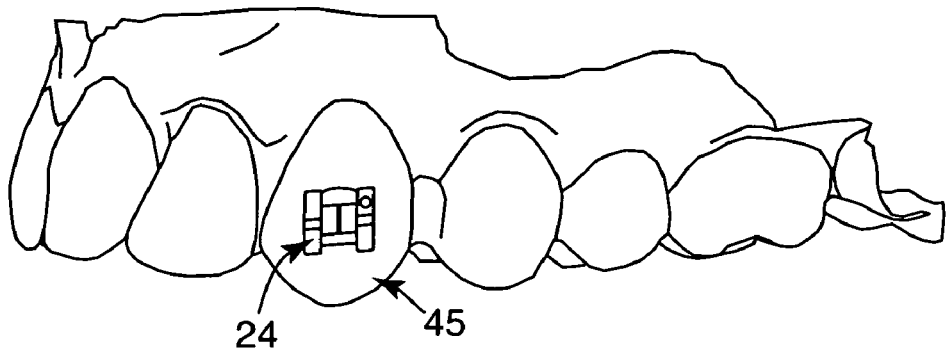
FIG. 10 is a schematic elevational view of the dental arch shown in FIG. 2 along with the appliance shown in FIGS. 3, 4 and 6, wherein the appliance has been placed on the tooth at a desired location and in a desired orientation.

FIG. 10 is an illustration of the bracket 24 that has been placed at the desired location on the cuspid tooth 45. In this view, the bracket 24 is illustrated in its optimal orientation relative to the cuspid tooth 45 so that a close, mating fit between the base 26 and the tooth surface 47 is attained. The computer carrying out the method then virtually "detaches" the bracket 24 from the line-of-sight 38 so that other appliances may be placed on respective teeth as desired.

Figure 11:
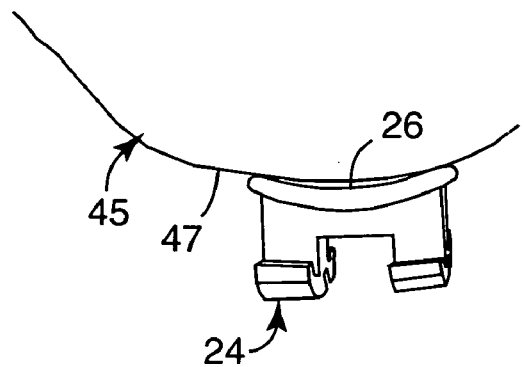
FIG. 11 is a fragmentary, enlarged top view, looking in an occlusal direction, of the appliance and cuspid tooth shown in FIG. 10, illustrating the fit of the base of the appliance against the facial surface of the tooth.

FIG. 11 is an enlarged, fragmentary top view of the bracket 24 and the adjacent labial surface of the cuspid tooth 45. In this illustration, it can be observed that a small gap is present between the base 26 and the surface 47 of the cuspid tooth 45 in a location near the middle of the base 26. The gap is present because of the difference in curvature between the tooth surface 47 and the base 26, even though the orientation of the bracket 24 relative to the cuspid tooth 45 has been selected by the method set out above in order to achieve a close fit between the bracket 24 and the tooth 45.

Figure 12:
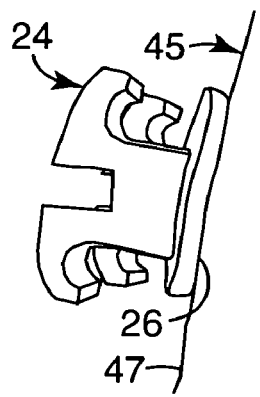
FIG. 12 is a view somewhat similar to FIG. 11 except that FIG. 12 is a side elevational view of the appliance, looking in a mesial direction.

FIG. 12 is an enlarged, side elevational view showing the bracket 24 and a portion of the cuspid tooth 45, looking in a mesial direction. In this view, the curvature of the base 26 closely matches the curvature of the adjacent section of the tooth 45 and no gap along the mesial edge of the base 26 is apparent.

Figure 13:
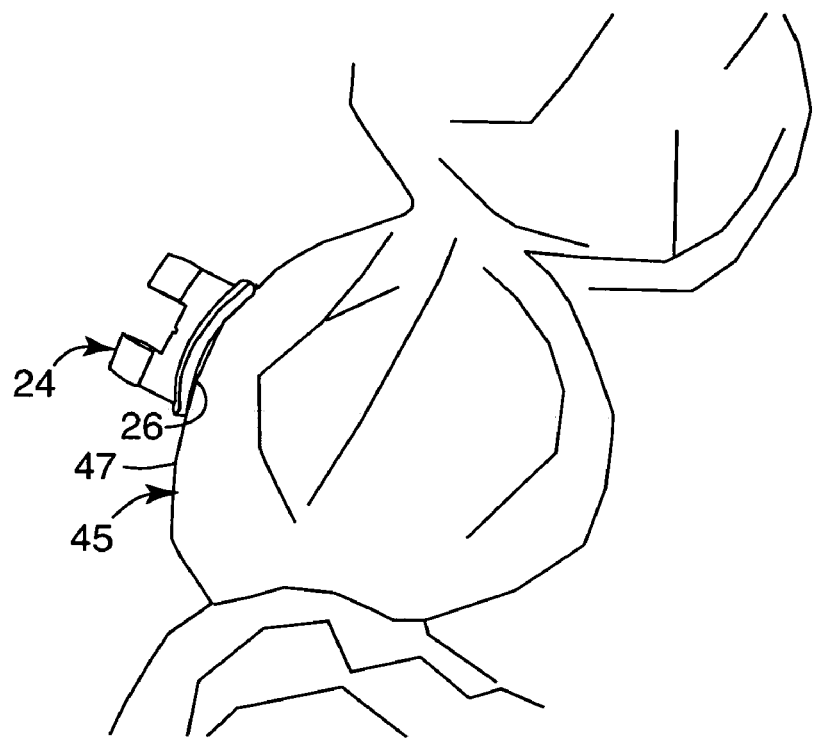
FIG. 13 is a view somewhat similar to FIGS. 11 and 12, except that FIG. 13 is a bottom view of the appliance, looking in a gingival direction.

FIG. 13 is an enlarged bottom view of the bracket 24 and the cuspid tooth 45, looking at the tooth in a gingival direction. The curvature of the base 26 is somewhat different than the curvature of adjacent portions of the tooth 45 in this view, and as a consequence, a slight gap is observed. However, the use of the method described above tends to optimize the relative orientation between the bracket 24 and the tooth 45 such that a relatively close fit is attained.

Optionally, the computer program carrying out the method described above may also enable the user to shift the appliance on the tooth to a preferred orientation, using translational movement along the surface of the tooth as well as rotative movement about its labio-lingual axis or the Z axis as shown, e.g., in FIG. 4. The user may shift the appliance manually (for example, by a click and drag motion of a computer mouse) or automatically (for example, by specifying that the archwire slot of the appliance should extend in a direction parallel to the occlusal plane and be located a certain distance from the occlusal edge of the tooth. Such adjustments are preferably carried out simultaneously with the steps set out above in FIG. 1, so that the appliance remains in an optimal fit with respect to the tooth surface as the adjustments are made.

Figure 14:
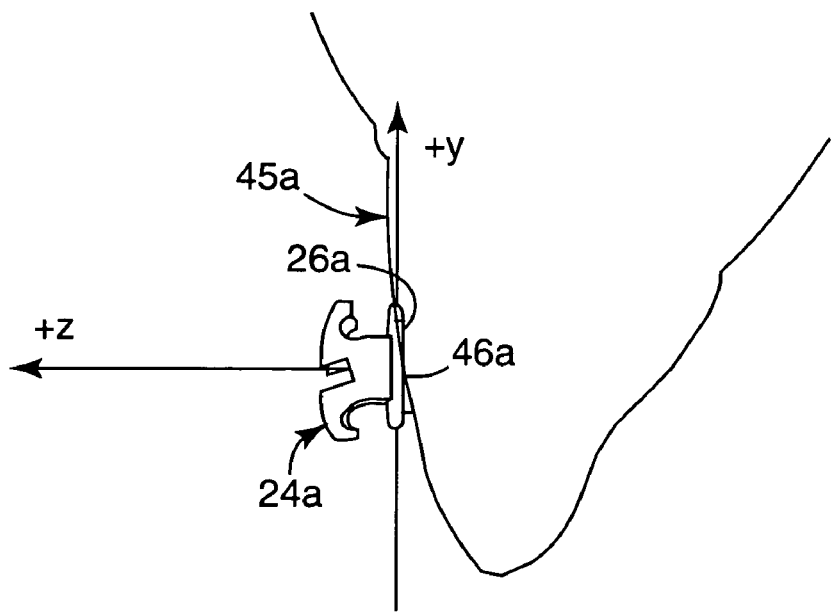
FIG. 14 is a view somewhat similar to FIG. 8 but showing a somewhat different representation of the relative orientations of the appliance and the tooth in accordance with another embodiment of the invention.

FIG. 14 is an illustration of an alternate embodiment of the invention, wherein the method is carried out as described above except the appliance is initially located next to the tooth surface. In particular, the center of a base 26a of a bracket 24a is placed in a location tangent to the facial axis point 46a in this embodiment. Consequently, as the bracket is rotated about its mesial-distal axis as exemplified above by Box 70, some of the sample points on the bracket base may exist on a lingual side of the facial surface of cuspid tooth 45a. As shown, other sample points may exist in a direction labially of the facial surface of cuspid tooth 45a.

The method described earlier in connection with FIGS. 2–13 is used in conjunction with the embodiment exemplified by FIG. 14 except that absolute values of the distances are calculated. In addition, in the final orientation of the bracket 24 relative to the tooth 45, the bracket 24 is translated in a buccolabial direction so that none of the sample points lie on a lingual side of the facial surface of the cuspid tooth 45.

A number of variations to the methods described above are also possible and will be apparent to those skilled in the art. For example, the method may be used in conjunction with appliances that are to be bonded to the lingual surfaces of the patient's teeth. Also, reference axes and points of reference (such as the facial axis point) may be different from those set out above.

Moreover, the method described above may be changed by varying the amount of rotative movement in accordance with the attained result. For example, the increment of rotative movement initially may be relatively large and then reduced in subsequent steps. For example, the amount of rotative movement can be reduced once a difference in sign is noted as determined in Box 76.

Other variations are also possible. Accordingly, the invention should not be deemed limited to the specific embodiments described above in detail, but instead only by a fair scope of the claims that follow along with their equivalents.

The invention claimed is:

1. A method of selecting a relative orientation of an orthodontic appliance and a tooth comprising:

providing a first relative orientation of the appliance and the tooth;

defining a first set of rays extending between a base of the appliance and the tooth when the appliance and the tooth are in the first relative orientation;

determining the distance along each ray between the base and the tooth when the appliance and the tooth are in the first relative orientation;

relatively moving the appliance and the tooth in an arc about a reference axis to a second relative orientation;

defining a second set of rays extending between the base and the tooth when the appliance and the tooth are in the second relative orientation;

determining the distance along each ray between the base and the tooth when the appliance and the tooth are in the second relative orientation;

quantifying the difference between the distances determined when the appliance and the tooth are in the first relative orientation and the distances determined when the appliance and the tooth are in the second relative orientation; and relatively moving the appliance and the tooth in an arc about the reference axis in a direction such that the quantified difference is reduced.

2. A method of selecting a relative orientation of an orthodontic appliance and a tooth according to claim 1 wherein the act of quantifying the difference between the distances determined when the appliance and tooth are in the first relative orientation to the distances when the appliance and tooth are in the second relative orientation includes the act of calculating a mean distance between the appliance and the tooth on at least one side of the reference axis when the appliance and tooth are in the first relative orientation and a mean distance between the appliance and the tooth on at least one side of the reference axis when the appliance and the tooth are in the second relative orientation.

3. A method of selecting a relative orientation of an orthodontic appliance and a tooth according to claim 1 wherein the act of quantifying the difference between the distances determined when the appliance and tooth are in the first relative orientation to the distances determined when the appliance and tooth are in the second relative orientation includes the act of calculating a root mean square distance between the appliance and the tooth on at least one side of the reference axis when the appliance and tooth are in the first relative orientation and a root mean square distance between the appliance and the tooth on at least one side of the reference axis when the appliance and the tooth are in the second relative orientation.

4. A method of selecting a relative orientation of an orthodontic appliance and a tooth according to claim 1 wherein the act of quantifying the difference between the distances determined when the appliance and tooth are in the first relative orientation to the distances determined when the appliance and tooth are in the second relative orientation includes the act of calculating a sum of the distances between the appliance and the tooth on at least one side of the reference axis when the appliance and tooth are in the first relative orientation and a sum of the distances between the appliance and the tooth on at least one side of the reference axis when the appliance and the tooth are in the second relative orientation.

5. A method of selecting a relative orientation of an orthodontic appliance and a tooth according to claim 1 and wherein the reference axis is generally perpendicular to the rays.

6. A method of selecting a relative orientation of an orthodontic appliance and a tooth according to claim 5 wherein the base has a center, and wherein the axis extends from the center.

7. A method of selecting a relative orientation of an orthodontic appliance and a tooth according to claim 6 wherein the axis extends in a generally mesial-distal direction.

8. A method of selecting a relative orientation of an orthodontic appliance and a tooth according to claim 6 wherein the axis extends in a generally occlusal-gingival direction.

9. A method of selecting a relative orientation of an orthodontic appliance and a tooth according to claim 1 wherein the reference axis is a first axis, and including the act of relatively moving the appliance and the tooth about a second axis, wherein the first axis and the second axis are both generally perpendicular to the rays, and wherein the first axis is generally perpendicular to the second axis.

10. A method of selecting a relative orientation of an orthodontic appliance and a tooth according to claim 9 wherein the first axis is a mesial-distal reference axis, and wherein the second axis is an occlusal-gingival reference axis.

11. A method of selecting a relative orientation of an orthodontic appliance and a tooth according to claim 1 and including the act of aligning the center of the base of the appliance with a mid-sagittal reference plane extending through the tooth.

12. A method of selecting a relative orientation of an orthodontic appliance and a tooth according to claim 1 and including the act of aligning the center of the base of the appliance with a mid-lateral reference plane extending through the tooth.

13. A method of selecting a relative orientation of an orthodontic appliance and a tooth according to claim 1 and including the act of aligning the appliance by use of a pair of intersecting crosshairs.

14. A method of selecting a relative orientation of an orthodontic appliance and a tooth according to claim 13 wherein the crosshairs intersect at an angle other than 90 degrees.

15. A method of selecting a relative orientation of an orthodontic appliance and a tooth comprising:
  providing a first relative orientation of the appliance and the tooth;
  defining a first set of rays extending between a base of the appliance and the tooth when the appliance and the tooth are in the first relative orientation;
  determining the distance along each ray between the base and the tooth when the appliance and the tooth are in the first relative orientation;
  providing a second relative orientation of the appliance and the tooth;
  defining a second set of rays extending between the base and the tooth when the appliance and the tooth are in the second relative orientation;
  determining the distance along each ray between the base and the tooth when the appliance and the tooth are in the second relative orientation; and
  comparing the distances when the appliance and the tooth are in the first relative orientation to the distances when the appliance and the tooth are in the second relative orientation in order to select the orientation that corresponds to a closer fit between the base of the appliance and the tooth.

16. A method of selecting a relative orientation of an orthodontic appliance and a tooth according to claim 15 wherein the act of comparing the distances when the appliance and tooth are in the first relative orientation to the distances when the appliance and tooth are in the second relative orientation includes the act of calculating a mean distance between at least a portion of the base of the appliance and the tooth when the appliance and tooth are in the first relative orientation and a mean distance between at least a portion of the base of the appliance and the tooth when the appliance and the tooth are in the second relative orientation.

17. A method of selecting a relative orientation of an orthodontic appliance and a tooth according to claim 15 wherein the act of comparing the distances when the appliance and tooth are in the first relative orientation to the distances when the appliance and tooth are in the second relative orientation includes the act of calculating a root mean square distance between at least a portion of the base of the appliance and the tooth when the appliance and tooth are in the first relative orientation and a root mean square distance between at least a portion of the base of the appliance and the tooth when the appliance and the tooth are in the second relative orientation.

18. A method of selecting a relative orientation of an orthodontic appliance and a tooth according to claim 15 wherein the act of comparing the distances when the appliance and tooth are in the first relative orientation to the distances when the appliance and tooth are in the second relative orientation includes the act of calculating a sum of the distances between at least a portion of the base of the appliance and the tooth when the appliance and tooth are in the first relative orientation and a sum of the distances between at least a portion of the base of the appliance and the tooth when the appliance and the tooth are in the second relative orientation.

19. A method of selecting a relative orientation of an orthodontic appliance and a tooth according to claim 15 and including the act of relatively moving the appliance and the tooth about an axis generally perpendicular to the rays in order to move the appliance in the first orientation to the second orientation.

20. A method of selecting a relative orientation of an orthodontic appliance and a tooth according to claim 19 wherein the base has a center, and wherein the axis extends from the center.

21. A method of selecting a relative orientation of an orthodontic appliance and a tooth according to claim 20 wherein the axis extends in a generally mesial-distal direction.

22. A method of selecting a relative orientation of an orthodontic appliance and a tooth according to claim 20 wherein the axis extends in a generally occlusal-gingival direction.

23. A method of selecting a relative orientation of an orthodontic appliance and a tooth according to claim 15 and including the act of relatively moving the appliance and the tooth about a first axis and subsequently relatively moving the appliance and the tooth about a second axis, wherein the first axis and the second axis are both generally perpendicular to the rays, and wherein the first axis is generally perpendicular to the second axis.

24. A method of selecting a relative orientation of an orthodontic appliance and a tooth according to claim 23 wherein the first axis is a mesial-distal reference axis, and wherein the second axis is an occlusal-gingival reference axis.

25. A method of selecting a relative orientation of an orthodontic appliance and a tooth according to claim 15 and including the act of aligning the center of the base of the appliance with a mid-sagittal reference plane extending through the tooth.

26. A method of selecting a relative orientation of an orthodontic appliance and a tooth according to claim 15 and including the act of aligning the center of the base of the appliance with a mid-lateral reference plane extending through the tooth.

27. A method of selecting a relative orientation of an orthodontic appliance and a tooth comprising:
   defining a set of rays extending between the appliance and a tooth, wherein each ray extends from a point located on the base of the appliance and the point located on the tooth;
   determining the distance along the rays between each point on the base and each corresponding point on the tooth; and
   relatively moving the appliance and the tooth in an arc about a reference axis in a direction such that the sum of the differences between each distance and the mean of the distances is reduced.

28. A method of selecting a relative orientation of an orthodontic appliance and a tooth according to claim 27 wherein the method includes the act of calculating a mean distance of at least some of the distances determined when the appliance and tooth are in the first relative orientation and a mean distance of at least some of the distances determined when the appliance and the tooth are in the second relative orientation, and wherein the act of relatively moving the appliance and the tooth is carried out by relatively moving the appliance and the tooth in a direction that reduces the sum of the mean distances.

29. A method of selecting a relative orientation of an orthodontic appliance and a tooth according to claim 27 wherein the method includes the act of calculating a root mean square distance of at least some of the distances determined when the appliance and tooth are in the first relative orientation and a root mean square distance of at least some of the distances determined when the appliance and the tooth are in the second relative orientation, and wherein the act of relatively moving the appliance and the tooth is carried out by relatively moving the appliance and the tooth in a direction that reduces the sum of the root mean square distances.

30. A method of selecting a relative orientation of an orthodontic appliance and a tooth according to claim 27 wherein the method includes the act of calculating a first sum of at least some of the distances when the appliance and tooth are in the first relative orientation and a second sum of at least some of the distances when the appliance and the tooth are in the second relative orientation, and wherein the act of relatively moving the appliance and the tooth is carried out by relatively moving the appliance and the tooth in a direction that reduces the difference between the first and second sums.

31. A method of selecting a relative orientation of an orthodontic appliance and a tooth according to claim 27 and including the act of relatively moving the appliance and the tooth about an axis generally perpendicular to the rays in order to move the appliance in the first relative orientation to the second relative orientation.

32. A method of selecting a relative orientation of an orthodontic appliance and a tooth according to claim 31 wherein the base has a center, and wherein the axis extends from the center.

33. A method of selecting a relative orientation of an orthodontic appliance and a tooth according to claim 31 wherein the axis extends in a generally mesial-distal direction.

34. A method of selecting a relative orientation of an orthodontic appliance and a tooth according to claim 32 wherein the axis extends in a generally occlusal-gingival direction.

35. A method of selecting a relative orientation of an orthodontic appliance and a tooth according to claim 27 and including the act of relatively moving the appliance and the tooth in an arc about a second reference axis, and further including the act of determining the distances along the rays between each point on the base and each corresponding point on the tooth when the appliance and the tooth are in a first and second relative orientation with respect to the second reference axis.

36. A method of selecting a relative orientation of an orthodontic appliance and a tooth according to claim 27 wherein the rays extend in generally parallel directions.

37. A method of selecting a relative orientation of an orthodontic appliance and a tooth according to claim 27 and including the act of aligning the center of the base of the appliance with a mid-sagittal reference plane extending through the tooth.

38. A method of selecting a relative orientation of an orthodontic appliance and a tooth according to claim 27 and including the act of aligning the center of the base of the appliance with a mid-lateral reference plane extending through the tooth.

39. A method of selecting a relative orientation of an orthodontic appliance and a tooth according to claim 27 and including the act of relatively moving the appliance and the tooth in an arc about a second reference axis in a direction such that the sum of the differences between each distance and the mean of the distances is reduced.

40. A method of selecting a relative orientation of an orthodontic appliance and a tooth according to claim 27 wherein the appliance is also moved along the surface of the tooth and/or moved in a rotative direction about its labio-lingual axis to a user-specified orientation.

41. A computer readable storage medium having program code stored thereon that, when executed by a computer, performs any of the methods of claims 1–40.

* * * * *